United States Patent [19]

De Vincentiis

[11] Patent Number: 4,469,691
[45] Date of Patent: Sep. 4, 1984

[54] HEXAMETHYLENETETRAMINE-N-ACETYL-THIAZOLIDINE-4-CARBOXYLATE, A PROCESS FOR ITS PREPARATION AND A PHARMACEUTICAL COMPOSITION CONTAINING IT

[75] Inventor: Leonardo De Vincentiis, Rome, Italy

[73] Assignee: Ausonia Farmaceutici s.r.l., Rome, Italy

[21] Appl. No.: 441,161

[22] Filed: Nov. 12, 1982

[30] Foreign Application Priority Data

Mar. 1, 1982 [IT] Italy .................................. 19900 A/82

[51] Int. Cl.³ .................. C07D 487/18; A61K 31/425
[52] U.S. Cl. .................................... 424/249; 544/185; 544/186
[58] Field of Search .................. 544/185, 186; 424/249

[56] References Cited

U.S. PATENT DOCUMENTS 3,669,987 6/1972 Sato et al. ............................ 544/185
4,001,231 1/1977 Diamond ............................. 544/186

Primary Examiner—John M. Ford
Attorney, Agent, or Firm—Walter H. Schneider

[57] ABSTRACT

Hexamethylenetetramine-N-acetyl-thiazolidine-4-carboxylate having formula (I)

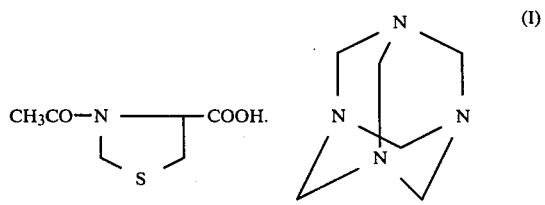

is endowed with antibacterial and mucosecretolytic properties. These properties along with the very low toxicity of the compound (I) make it particularly suited for the chemotherapeutical treatment of the affections of the urinary and intestinal tracts, and for the treatment of bladder and intestinal catarrhs.

3 Claims, No Drawings

HEXAMETHYLENETETRAMINE-N-ACETYL-THIAZOLIDINE-4-CARBOXYLATE, A PROCESS FOR ITS PREPARATION AND A PHARMACEUTICAL COMPOSITION CONTAINING IT

DESCRIPTION OF THE INVENTION

The present invention relates to a novel compound, namely hexamethylenetetramine-N-acetyl-thiazolidine-4-carboxylate, having formula (I)

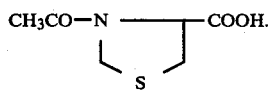 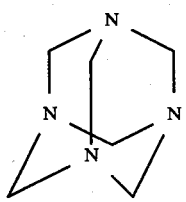

Hexamethylenetretramine is a known drug which has been used for years as chemotherapeutical agent for the treatment of infections of the urinary tract: hexamethylenetetramine is readily absorbed and eliminated unchanged in the urine (90%); in acid urine hexamethylenetetramine is converted to its pharmacologically active metabolite, namely formaldehyde (about 15% of the whole dose); (Martindale—The Extra Pharmacopoeia—27th Edition, page 1006).

During the chemotherapeutical treatment with hexamethylenetetramine the patient's urine must be rendered acid: it is also to this end that, for therapeutical treatments, hexamethylenetetramine salts are used, the best known of which are the hippurate and mandelate.

Hexamethylenetetramine hippurate, however, is contraindicated in patients with hepatic insufficiency and requires the use of acidifying agents whenever urea-splitting bacteria are present in the urine. Acidifying substances must constantly be used whenever hexamethylenetretramine mandelate is given for therapeutical purposes.

It has been found that hexamethylenetetramine-N-acetyl-thiazolidine-4-carboxylate (I) not only possesses a higher antibacterial activity than hexamethylenetetramine but is also endowed with remarkable mucosecretolytic properties and protective activity against liver affections which makes it particularly suited also for the treatment of patients with acute and chronic liver diseases.

Therefore, the present invention also relates to pharmaceutical compositions containing, as the active agent, the compound (I).

Lastly, this invention relates to a process for preparing the compound (I), characterized by reacting in polar solvents N-acetyl-thiazolidine-4-carboxylic acid and hexamethylenetetramine in substantially stoichiometric amounts, and isolating the salt (I) by precipitation carried out with non-polar solvents. As polar solvents, lower alkanols such as methanol, ethanol and isopropanol are preferably used. Preferred non-polar solvents are diethyl- and diisopropyl ether. Alternatively, the salt (I) can be isolated by solvent evaporation.

The following example illustrates the process of this invention, without limiting in any way the scope thereof.

EXAMPLE

N-acetyl-thiazolidine-4-carboxylic acid (1 mole) and hexamethylenetetramine (urotropine) (1 mole) are dissolved in 1 liter of methanol. The resulting mixture is refluxed for 30 minutes and then about 800 mls. of methanol are distilled off. Isopropyl ether is then added until the mixture becomes markedly cloudy. The resulting mixture is left to stand in ice until complete precipitation occurs (from 10 to 48 hours).

The crystalline product is filtered off and dried under vacuum at about 30° C. The yield is almost quantitative.

The salt (I) thus obtained has melting point 240°–245° C. (dec.); it is extremely water-soluble, soluble in lower alkanols and insoluble in acetone and ether.

Elementary analysis $C_{12}H_{21}N_5O_3S$ (Mol. weight: 315.28). calculated: C=45.71%; H=6.71%; N=22.20%; found: C=45.58%; H=6.79%; N=22.03%.

IR spectrum (nujol mull; absorption bands are expressed in $cm^{-1}$):

| stretch | O—H | 3400 |
|---|---|---|
| stretch | C—H thiazolidine | 2980–2810 |
| stretch | C—H urotropine | 2460–2600 |
| stretch | C=H amide and carboxylate | 1650–1620 |

$H^1$ NMR spectrum (detected in hexadeuterodimethyl sulfoxide, inner standard TMS; chemical shifts are expressed in δ): 2.1 (d, 3H, CO—CH$_3$); 3.1–3.4 (m, 2H, S—CH$_2$—COOH); 4.3–4.9 (m, 15H, 12H of urotropine; N—CH$_2$—S; N—CH—COOH); 7.5 (s, 1H mobile).

The biological characteristics of the compound (I) (henceforth referred to, for the sake of brevity, with the abbreviation AFP 829) are illustrated as follows:

TOXICITY the acute toxicity of AFP 289 in comparison with thiazolidine-4-carboxylic acid (TCA) and hexamethylenetetramine (EMTA) was determined by the oral route in Swiss mice and Wistar rats and calculated according to the Litchfield and Wilcoxon method (J. Pharm. Exp. Therap. 96, 99–113 (1949)).

LD$_{50}$, which is reported in Table 1, shows that the compound under examination possesses very low toxicity.

TABLE 1

| Species | Administration route | LD$_{50}$ (mg/Kg) Afp 289 | EMTA | TCA |
|---|---|---|---|---|
| mouse | oral | 1350 | 1500 | 400 |
| rat | oral | 2100 | 1050 | 800 |

ANTIBACTERIAL ACTIVITY

"In vitro" activity

The "in vitro" antibacterial activity of AFP 829 in comparison with hexamethylenetetramine (EMTA) was assessed against 90 strains of different Gram-positive and Gram-negative bacterial species which had been recently isolated from clinical specimens, by determining the minimum inhibitory concentration (M.I.C.), i.e. the lowest antibacterial concentration liable to inhibit the growth of bacteria.

To carry out these experiments, the following bacterial strains were used:

Gram-positive (35 strains):

| Staphylococcus aureus | (15 strains) |
|---|---|
| Streptococcus pyogenes | (15 strains) |
| Streptococcus faecalis | (5 strains) |
| Gram-negative (55 strains): | |
| Salmonella spp | (10 strains) |
| Pseudomonas aeruginosa | (10 strains) |
| Proteus spp | (10 strains) |
| E. coli | (10 strains) |
| Klebsiella spp | (7 strains) |
| Serratia spp | (5 strains) |
| Citrobacter spp | (3 strains). |

As culture medium, Mueller Hinton Agar at pH 5.5 was used. The compounds under examination were dissolved in and diluted by sterile saline; 1 ml of the diluted solutions thus obtained was poured in Petri's dishes and 19 ml of Mueller Hinton Agar were subsequently added thereto.

The final hexamethylenetetramine (EMTA) concentrations were: 2000, 1000, 500, 250, 125, 62.5, 31.2, 15.6, 7.8 and 3.9 mcg/ml.

The AFP 829 concentrations were equimolar to those of EMTA.

The inoculation of bacteria was performed using a multi point inoculator and a 18 hour growth broth culture of each of the strains under examination. With this method the bacterial inoculum is equal to about $10^5$ colony-forming units (CFU) per point. Reading of the results was performed after cultivating the plates for 18 hours at 37° C.

The results are contained in Tables 2 and 3 where it can be observed that AFP 829 is active in comparison with all of the microorganisms used whether Gram-positive or Gram-negative; no microorganism proved to be resistant to concentrations higher than 125 mcg/ml and it can be noted that the standard drug, EMTA, showed itself to be slightly less active.

TABLE 2

| Bacterial strain | Number of strains | Drug | Concentrations (°) in mcg/ml |||||||||| 
|---|---|---|---|---|---|---|---|---|---|---|---|---|
| | | | ≦3.9 | 7.8 | 15.6 | 31.2 | 62.5 | 125 | 250 | 500 | 1000 | ≧2000 |
| Salmonella | 10 | EMTA | | | | | 9 | 10 | | | | |
| | | AFP 829 (*) | | | | 1 | 10 | | | | | |
| Pseudomonas | 10 | EMTA | | | | | 10 | | | | | |
| | | AFP 829 (*) | | | | | 10 | | | | | |
| Proteus | 10 | EMTA | | | | | 10 | | | | | |
| | | AFP 829 (*) | | | | 3 | 10 | | | | | |
| E. coli | 10 | EMTA | | | | | 8 | 10 | | | | |
| | | AFP 829 (*) | | | | | 10 | | | | | |
| Klebsiella | 7 | EMTA | | | | | 6 | | | | | |
| | | AFP 829 (*) | | | | | 7 | | | | | |
| Serratia | 5 | EMTA | | | | | 4 | 5 | | | | |
| | | AFP 829 (*) | | | | | 4 | 5 | | | | |
| Citrobacter | 3 | EMTA | | | | | 2 | 3 | | | | |
| | | AFP 829 (*) | | | | | 3 | | | | | |

(°) EMTA
(*) The AFP 829 concentrations were equimolar to those of EMTA.

TABLE 3

| Bacterial strain | Number of strains | Drug | Concentrations (°) in mcg/ml |||||||||| 
|---|---|---|---|---|---|---|---|---|---|---|---|---|
| | | | ≦3.9 | 7.8 | 15.6 | 31.2 | 62.5 | 125 | 250 | 500 | 1000 | ≧2000 |
| S. aureus | 15 | EMTA | | | | | | 10 | 14 | 15 | | |
| | | AFP 829 (*) | | | | | | 13 | 15 | | | |
| Streptococcus | 15 | EMTA | | | | 7 | | 11 | 13 | 14 | 15 | |
| | | AFP 829 (*) | | | | 5 | | 12 | 15 | | | |
| Enterococcus | 5 | EMTA | | | | | | 4 | 5 | | | |
| | | AFP 829 (*) | | | | 1 | | 5 | | | | |

(°) EMTA
(*) The AFP 829 concentrations were equimolar to those of EMTA.

"In vivo" Activity
Urinary Excretion

The urinary excretion of AFP 829 compared with the excretion of hexamethylentetramine (EMTA) was determined in overnight fasted Sprague Dawley rats weighing an average of 300 g. The compounds under examination were dissolved in tap water at equimolecular doses: AFT 829 = 135 mg/rat; EMTA = 60 mg/rat.

Each group of animals received the substances i.p. in 50 ml of sterile saline; the animals were placed in metabolic cages with free access to water. Urine samples were collected at the following intervals:

| |
|---|
| 0–1.30 hr |
| 1.30–2.30 hr |
| 2.30–4.30 hr |
| 4.30–6.30 hr. |

1 ml of nutrient broth at pH 5.5, containing approximately $1.10^{-5}$ colony-forming units of a strain of Ps. aeruginosa sensitive to the action of both substances, was added to 1 ml of the urine or the standard solution of the two drugs dissolved in distilled water.

Standard and urine samples were sequentially diluted twofold by means of the same broth containing the microorganisms until a 1:2048 dilution was achieved.

After overnight incubation at 37° C. the maximum dilution (limit dilution) of the substances or samples inhibiting bacterial growth was determined.

Therefore the concentration of the substances in the urine samples was determined using the formula below:

$$\frac{\text{Limit dilution of the urine under examination}}{\text{Limit dilution of the standard solution}} \times \text{Initial concentration of the standard solution}$$

The tests show that both substances are excreted in the urine in the biologically active form; however, AFP 829 is excreted with a markedly higher degree of antibacterial activity than EMTA used as reference standard compound. See Table 4.

TABLE 4

Urinary excretion in Sprague-Dawley rats of the orally administered AFP 829 molecule

| Time interval (hours) | mcg/ml of urine | | Total excreted amount (mcg) | | % excreted | | % total excreted | |
|---|---|---|---|---|---|---|---|---|
| | AFP 829 | EMTA | AFP 829 | EMTA | AFP 829 | EMTA | AFP 829 | EMTA |
| 0–1.30 | 2000 | 1000 | 3000 | 1600 | 1.6 | 0.88 | | |
| 1.30–2.30 | 4000 | 4000 | 12800 | 11200 | 7.0 | 6.2 | 17.0 | 11.4 |
| 2.30–4.30 | 4000 | 2000 | 14000 | 7200 | 7.6 | 4.0 | | |
| 4.30–6.30 | 1000 | 1000 | 1000 | 800 | 0.54 | 0.44 | | |

MUCOSECRETOLYTIC ACTIVITY

Mucosecretolytic activity was determined in male Wistar rats after AFP 829 administration given via the oral route. The method described by H. Mawatari was used for the determination [H. Mawatari, Kagoshima Daiagaku, Igaku Zasshi 27, 561 (1976)]. A drug of known activity—carboxymethylcysteine—was used as the reference standard.

The results thus obtained are given in the Table below.

TABLE 5

| Compound | Dose given mg/Kg/p.o | No. of animals | % increase of sodium fluorescein compared with controls |
|---|---|---|---|
| AFP 829 | 250 | 10 | 96.1 |
| Carboxymethylcysteine | 250 | 10 | 33.4 |

The above values show that AFP 829 possesses powerful mucosecretolytic activity, markedly higher than the standard substance (carboxymethylcysteine).

PHARMACOKINETICS

The tests carried out on laboratory animals after oral administration of equimolecular doses of AFP 829 and EMTA showed that AFP 829 administration permits a faster absorption and a faster urinary excretion of EMTA to occur with respect to the EMTA-treated controls.

AFT 829 and EMTA selectively occur in the urine along with the active metabolites thereof.

The above emphasizes the usefulness of the compound (I) as a chemotherapeutic agent of the urinary and intestinal tracts.

The present invention also relates to all the applicable industrial aspects connected with the use of AFP 829 as an agent for the treatment of bacterial affections of the urinary and intestinal tracts, and for the treatment of bladder and intestinal catarrhs. Therefore, an essential aspect of the invention is represented by the pharmaceutical compositions containing predetermined quantities of AFP 829. The compound of the present invention can be administered via the oral route, for instance in the form of tablets, pills, capsules, sachets, syrups etc.

The compositions below are described as an example:

(a) tablets and pills containing 500–1000 mg of AFP 829, in addition to excipients, disintegrators etc. commonly used in the pharmaceutical art;

(b) 500 mg capsules of AFP 829;

(c) mono-dose sachets, each containing 500–1000 mg of AFP 829;

(d) 5–10% syrup/suspension/drops of AFT 829, with sweeteners, flavouring agents, preservatives etc. commonly used in the pharmaceutical art.

What is claimed is:

1. Hexamethylenetetramine-N-acetylthiazolidine-4-carboxylate, having formula (I)

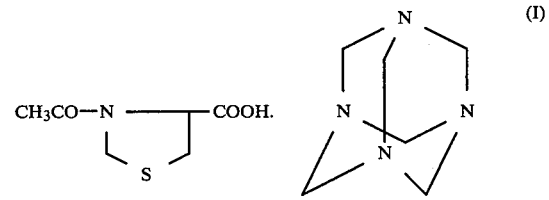

2. A process for preparing the compound (I) of claim 1, characterized by reacting in polar solvents N-acetyl-thiazolidine-4-carboxylic acid and hexamethylenetetramine in substantially stoichiometric amounts, and isolating the salt (I) by precipitating it with the addition of non-polar solvents.

3. A pharmaceutical composition for the chemotherapeutical treatment of affections of the urinary and intestinal tracts and for the treatment of bladder and intestinal catarrhs, comprising as the active agent an effective amount of hexamethylenetetramine-N-acetyl-thiazolidine-4-carboxylate of formula I in admixture with a pharmaceutically acceptable carrier.

* * * * *